United States Patent [19]

Storz

[11] Patent Number: 5,088,819
[45] Date of Patent: Feb. 18, 1992

[54] ENDOSCOPE, PARTICULARLY INDUSTRIAL ENDOSCOPE

[76] Inventor: Karl Storz, Auf dem Schildrain 39, 7200 Tuttlingen, Fed. Rep. of Germany

[21] Appl. No.: 517,867

[22] Filed: May 2, 1990

[30] Foreign Application Priority Data

Dec. 30, 1989 [DE] Fed. Rep. of Germany ....... 3943403

[51] Int. Cl.⁵ ............................................. G01B 11/00
[52] U.S. Cl. .................................................. 356/241
[58] Field of Search ............................ 356/241; 128/4

[56] References Cited

U.S. PATENT DOCUMENTS 4,078,864  3/1978  Howell ................................. 356/241
4,617,915 10/1986  Arakawa ................................ 128/4
4,928,699  5/1990  Sasai ..................................... 128/4

Primary Examiner—Richard A. Rosenberger
Attorney, Agent, or Firm—William A. Drucker

[57] ABSTRACT

An endoscope which includes an endoscope shaft and rotatable about the shaft axis, an eyepiece secured to and rotatable with the endoscope shaft about the axis of the endoscope shaft, a gear secured to and rotatable with the eyepiece and the endoscope shaft, an endoscope grip secured to the said gear, the gear positioned relative to the endoscope grip to permit manual holding of the grip and rotation of the gear with the same hand and a light guide for providing light to the endoscope shaft.

5 Claims, 1 Drawing Sheet

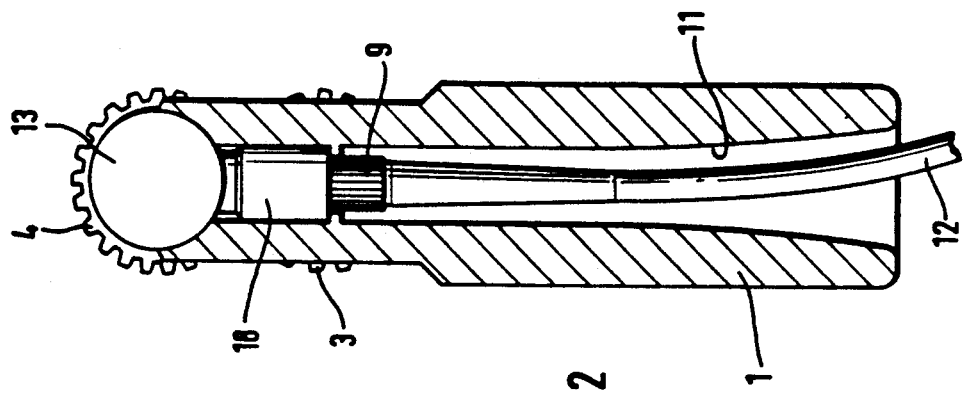
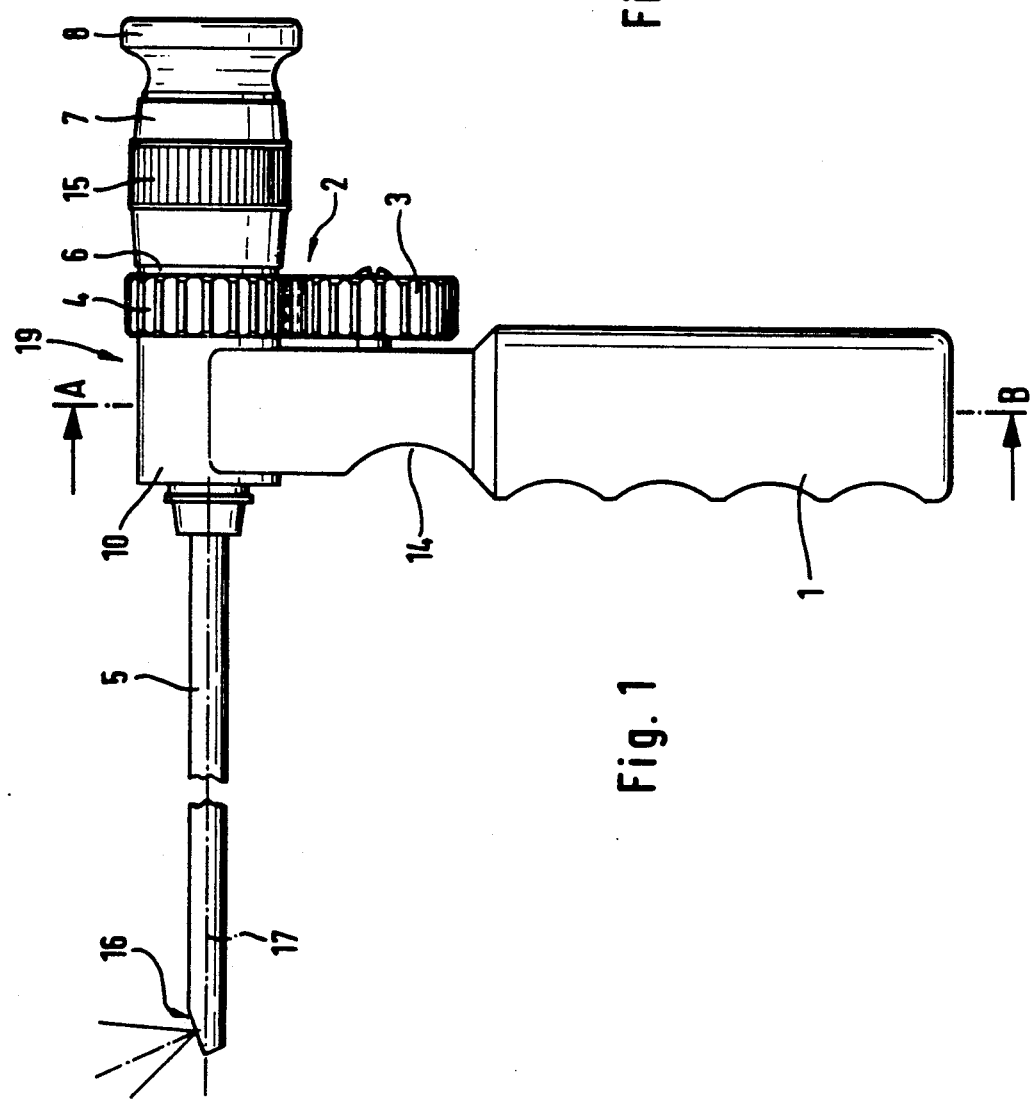

ENDOSCOPE, PARTICULARLY INDUSTRIAL ENDOSCOPE

BACKGROUND OF THE INVENTION

1. Field of the Invention

The invention relates to an endoscope.

2. Brief Description of The Prior Art

Such endoscopes are, inter alia, used for inspecting the advance of wear in turbines or motors, in that the endoscopes are inserted through a bore provided for this purpose in the combustion chambers and the like. By means of a special suction mechanism in the endoscope, it is also possible to clean these parts. For this purpose it is necessary to frequently rotate the endoscopes about their longitudinal axis, so that suction can be systematically applied to certain areas. If the operator has both hands free for this operation, it can take place without any difficulties. However, it frequently occurs that the endoscope must be held with one hand and the second hand has to manipulate the tool, so that this activity involves certain problems.

SUMMARY OF THE INVENTION

The purpose of the invention is to so improve the endoscope that one-handed operation is possible.

According to the invention this problem is solved by providing an endoscope comprising an endoscope shaft having an axis which is rotatable about the axis. An eyepiece is secured to and rotatable with the endoscope shaft about the axis of the endoscope shaft. A gear is secured to and rotatable with the eyepiece and the endoscope shaft. An endoscope grip is secured to the gear, the gear being positioned relative to the endoscope grip to permit manual holding of the grip and rotation of the gear with the same hand. The endoscope is provided with a light guide for providing light to the endoscope shaft. Thus, the operator is able to use the thumb of the hand, so that one-handed operation is possible.

It is also possible to use a gear other than that described hereinafter. For example, it is possible to move backward and forward with the thumb a rack, which engages in a second pinion.

BRIEF DESCRIPTION OF THE DRAWINGS

The invention is described in greater detail hereinafter relative to a non-limitative embodiment and the attached drawings, wherein:

FIG. 1 is a side view of the preferred embodiment.

FIG. 2 is a section along line A-B of FIG. 1.

DESCRIPTION OF THE PREFERRED EMBODIMENT

FIG. 1 shows to the left the endoscope shaft 5 with its lens 16 which can be rotated about the longitudinal axis 17, as will be explained hereinafter. The endoscope shaft 5 can also contain a suction mechanism for sucking off soot particles and the like. This is not shown in detail here because such endoscopes are well known. Further to the right it is possible to see a thick sleeve 10, which is fixed to the upper part of the grip or handle 1.

The grip or handle 1 located further down has in its upper area a wall opening 14 permitting the assembly and disassembly of the fibre optic light guide 12 according to FIG. 2 and as will be explained hereinafter.

Further to the right it is possible to see the first pinion 3, which is constructed in such a way that it can be operated by the hand embracing the grip 1. This first pinion 3 engages in a second pinion 4 of gear 2, which is fixed to a rotary sleeve 6 of headpiece 19.

Further to the right is a knurled portion 15, which serves to adjust the eyepiece 7 with eye muscle 8 separately from the rotary sleeve 6. Thus, with respect to the rotary sleeve 6, the eyepiece 7 can be additionally adjusted for sharp setting purposes.

In addition, the second pinion 4 is fixed together with the rotary sleeve 6 to the endoscope shaft 5 and also to the eyepiece 7.

If the pinion 3 is now turned by the operator's thumb, then, as a result of the tooth system, the torque is transferred to the second pinion 4, so that all the above parts, with the exception of the fixed endoscope sleeve 10, are rotated.

The bottom of FIG. 2 shows that the grip 1 has a longitudinal bore 11, in which the light guide 12 is screwed with knurled-head screw 9 to the connecting piece 18. This assembly point is accessible through wall opening 14 according to FIG. 1.

At the same level it is possible to see few a teeth of the first pinion 3, which project to the left and right over the grip 1. It is not possible to see the second pinion here, which has a somewhat smaller diameter than the first pinion 3.

Further toward the top it is possible to see a stopring 13, which is connected in manner not shown to the light guide in the endoscope shaft 5. This ensures a reliable transmission of light from the connecting piece 18 to the stopring 13, on turning the endoscope together with endoscope shaft 5, sleeve 6 and the remaining parts. It is also possible to ensure in any random rotation position a good transfer of light energy from connecting piece 18 to stopring 13 and therefore to the light guide in the endoscope shaft 5.

The assembly and disassembly of the light guide 12 with respect to the knurled-head screw 9 on connecting piece 18 takes place through the opening 14 according to FIG. 1, as stated hereinbefore.

The invention leads to the major advantage of one-handed operation. Thus, using the same hand as is gripping the grip 1, the operator preferably turns with the thumb the first pinion 3, without having to use the second hand.

The invention is not restricted to the represented and described embodiment. In fact those skilled in the art can make numerous modifications thereto. In particular, the possibility exists of replacing the first pinion 3 by a slide member with a rack, which is then forced upward or downward by the thumb in a guide, as a function of the rotation direction which is desired. This gives the possibility of systematically subjecting to suction action a specific area of a turbine or motor.

However, the invention is not limited to use in the industrial field. The need can also arise in the medical field for turning the endoscope shaft in the body cavity of the patient, e.g. in order to diagnose different areas.

I claim:

1. An endoscope comprising:
   (a) an endoscope shaft having an axis and rotatable about said axis;
   (b) an eyepiece secured to and rotatable with said endoscope shaft about said axis of said endoscope shaft;
   (c) a gear secured to and rotatable with said eyepiece and said endoscope shaft;

(d) an endoscope grip secured to said gear, said gear positioned relative to said endoscope grip to permit manual holding of said grip and rotation of said gear with the same hand; and (e) a light guide for providing light to said endoscope shaft.

2. An endoscope as set forth in claim 1 wherein said gear is a toothed gear which comprises two toothed pinions, the first one of said pinions secured to and rotatable with said eyepiece and said endoscope shaft and the second of said pinions rotatably coupled to said first pinion to form said gear therewith, said first pinion rotatable in response to rotation of said second pinion, said second pinion positioned relative to said endoscope grip to permit said manual holding of said grip and rotation of said second pinion with the same hand.

3. An endoscope as set forth in claim 2 further including a rotary sleeve secured to said first pinion, said first pinion enveloping said rotary sleeve.

4. An endoscope as set forth in claim 1 wherein said grip includes a longitudinal bore, a light guide positioned in said bore and a stop ring in said bore coupling said light guide to said endoscope shaft.

5. An endoscope as set forth in claim 1 wherein said grip includes a wall opening to said bore to provide access to the connection of said light guide to said stop ring.

* * * * *